United States Patent
Elmouelhi et al.

(10) Patent No.: US 8,945,114 B2
(45) Date of Patent: Feb. 3, 2015

(54) FLUID SENSOR FOR ABLATION THERAPY

(75) Inventors: Ahmed Elmouelhi, Minneapolis, MN (US); Paul S. Kratoska, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1675 days.

(21) Appl. No.: 11/789,996

(22) Filed: Apr. 26, 2007

(65) Prior Publication Data
US 2008/0269737 A1    Oct. 30, 2008

(51) Int. Cl.
*A61B 18/14* (2006.01)
*A61B 18/12* (2006.01)
*A61B 18/18* (2006.01)
*A61B 17/00* (2006.01)
*A61B 18/00* (2006.01)
*A61B 19/00* (2006.01)

(52) U.S. Cl.
CPC ......... *A61B 18/1477* (2013.01); *A61B 18/1233* (2013.01); *A61B 18/1815* (2013.01); *A61B 2017/00274* (2013.01); *A61B 2018/00011* (2013.01); *A61B 2018/00029* (2013.01); *A61B 2018/00083* (2013.01); *A61B 2018/00196* (2013.01); *A61B 2018/00517* (2013.01); *A61B 2018/00547* (2013.01); *A61B 2018/00577* (2013.01); *A61B 2018/00642* (2013.01); *A61B 2018/00702* (2013.01); *A61B 2018/00726* (2013.01); *A61B 2018/00863* (2013.01); *A61B 2018/00982* (2013.01); *A61B 2018/1425* (2013.01); *A61B 2018/1472* (2013.01); *A61B 2018/1475* (2013.01); *A61B 2019/464* (2013.01); *A61B 2218/002* (2013.01)
USPC ................................. 606/38; 606/34; 606/41

(58) Field of Classification Search
CPC ........... A61B 2018/00863; A61B 2018/00702; A61B 2018/00477; A61B 2018/00708
USPC .................................................. 606/45–46, 49
See application file for complete search history.

(56) References Cited

U.S. PATENT DOCUMENTS

| | | | |
|---|---|---|---|
| 4,653,987 | A | 3/1987 | Tsuji et al. |
| 5,345,362 | A | 9/1994 | Winkler |
| 5,435,805 | A | 7/1995 | Edwards et al. |
| 5,454,782 | A | 10/1995 | Perkins |

(Continued)

OTHER PUBLICATIONS

Birch et al., "Transurethral Resection of Prostate Under Sedation and Local Anesthesia (Sedoanalgesia)," Urology, Aug. 1991 vol. XXXVIII, No. 2., pp. 113-118.

(Continued)

*Primary Examiner* — Jaymi Della
(74) *Attorney, Agent, or Firm* — Shumaker & Sieffert, P.A.

(57) ABSTRACT

The disclosure describes a method and a system that may be used to provide feedback regarding the flow of fluid during ablation therapy. The system includes a generator that generates energy to ablate at least a portion of a target tissue, a needle that delivers the energy to the target tissue, a return electrode that receives energy dispersed from the needle, a catheter that houses at least a portion of the needle, a pump that delivers a fluid to the target tissue via the catheter, a sensor that detects a fluid parameter indicative of at least one of flow or pressure of the fluid, and a processor that analyzes the fluid parameter detected by the sensor. The sensor may be located between the pump and the target tissue. The fluid parameter detected by the system may be pressure or flow. The system may be used to treat benign prostatic hypertrophy.

23 Claims, 5 Drawing Sheets

(56) References Cited

U.S. PATENT DOCUMENTS

| | | | |
|---|---|---|---|
| 5,458,597 A | 10/1995 | Edwards et al. | |
| 5,462,525 A * | 10/1995 | Srisathapat et al. | 604/67 |
| 5,470,308 A | 11/1995 | Edwards et al. | |
| 5,472,441 A | 12/1995 | Edwards et al. | |
| 5,507,743 A | 4/1996 | Edwards et al. | |
| 5,531,676 A | 7/1996 | Edwards et al. | |
| 5,536,267 A | 7/1996 | Edwards et al. | |
| D373,193 S | 8/1996 | Luther | |
| 5,582,588 A | 12/1996 | Sakurai et al. | |
| 5,588,960 A | 12/1996 | Edwards et al. | |
| 5,628,745 A * | 5/1997 | Bek | 606/38 |
| 5,660,529 A | 8/1997 | Hill | |
| D394,903 S | 6/1998 | Barkley et al. | |
| 5,807,395 A | 9/1998 | Mulier et al. | |
| 5,827,280 A | 10/1998 | Sandock et al. | |
| D402,758 S | 12/1998 | Barkley et al. | |
| 5,865,788 A | 2/1999 | Edwards et al. | |
| 5,871,481 A | 2/1999 | Kannenberg et al. | |
| D411,622 S | 6/1999 | Hall | |
| 5,964,756 A | 10/1999 | McGaffigan et al. | |
| 5,995,875 A | 11/1999 | Blewett et al. | |
| 6,071,280 A | 6/2000 | Edwards et al. | |
| 6,090,105 A | 7/2000 | Zepeda et al. | |
| 6,106,521 A | 8/2000 | Blewett et al. | |
| 6,113,594 A | 9/2000 | Savage | |
| 6,113,597 A | 9/2000 | Eggers et al. | |
| 6,129,726 A | 10/2000 | Edwards et al. | |
| D438,204 S | 2/2001 | Winkler | |
| D441,450 S | 5/2001 | Salvatori et al. | |
| 6,231,591 B1 | 5/2001 | Desai | |
| 6,235,022 B1 | 5/2001 | Hallock et al. | |
| 6,238,393 B1 | 5/2001 | Mulier et al. | |
| 6,241,702 B1 | 6/2001 | Lundquist et al. | |
| D447,241 S | 8/2001 | Deck | |
| 6,280,440 B1 | 8/2001 | Gocho | |
| 6,302,903 B1 | 10/2001 | Mulier et al. | |
| 6,315,777 B1 | 11/2001 | Comben | |
| 6,327,492 B1 | 12/2001 | Lemelson | |
| 6,402,742 B1 | 6/2002 | Blewett et al. | |
| 6,409,722 B1 | 6/2002 | Hoey et al. | |
| 6,440,128 B1 | 8/2002 | Edwards et al. | |
| 6,461,296 B1 | 10/2002 | Desai | |
| 6,464,661 B2 | 10/2002 | Edwards et al. | |
| 6,471,698 B1 | 10/2002 | Edwards et al. | |
| 6,497,705 B2 | 12/2002 | Comben | |
| 6,514,247 B1 | 2/2003 | McGaffigan et al. | |
| 6,526,320 B2 | 2/2003 | Mitchell | |
| D471,279 S | 3/2003 | Locke et al. | |
| 6,537,248 B2 | 3/2003 | Mulier et al. | |
| 6,537,272 B2 | 3/2003 | Christopherson et al. | |
| 6,551,300 B1 | 4/2003 | McGaffigan | |
| 6,580,948 B2 | 6/2003 | Haupert et al. | |
| 6,623,515 B2 | 9/2003 | Mulier et al. | |
| 6,632,221 B1 | 10/2003 | Edwards et al. | |
| 6,632,222 B1 | 10/2003 | Edwards et al. | |
| 6,638,275 B1 | 10/2003 | McGaffigan et al. | |
| 6,641,580 B1 | 11/2003 | Edwards et al. | |
| 6,642,274 B1 | 11/2003 | Neal | |
| 6,645,202 B1 | 11/2003 | Pless et al. | |
| 6,652,516 B1 | 11/2003 | Gough | |
| 6,659,105 B2 | 12/2003 | Burbank et al. | |
| 6,659,106 B1 | 12/2003 | Hovda et al. | |
| 6,669,685 B1 | 12/2003 | Rizoiu et al. | |
| 6,671,558 B1 | 12/2003 | Soykan et al. | |
| D484,981 S | 1/2004 | Faller et al. | |
| 6,673,063 B2 | 1/2004 | Brett | |
| 6,676,658 B2 | 1/2004 | Burbank et al. | |
| 6,678,554 B1 | 1/2004 | Sun et al. | |
| 6,685,702 B2 | 2/2004 | Quijano et al. | |
| 6,689,128 B2 | 2/2004 | Sliwa, Jr. et al. | |
| 6,690,976 B2 | 2/2004 | Fenn et al. | |
| 6,706,039 B2 | 3/2004 | Mulier et al. | |
| 6,719,755 B2 | 4/2004 | Sliwa, Jr. et al. | |
| 6,761,715 B2 | 7/2004 | Carroll | |
| 6,764,487 B2 | 7/2004 | Mulier et al. | |
| 6,770,070 B1 * | 8/2004 | Balbierz | 606/41 |
| 6,805,128 B1 | 10/2004 | Pless et al. | |
| 6,805,129 B1 | 10/2004 | Pless et al. | |
| D499,183 S | 11/2004 | Vaisnys et al. | |
| 6,814,712 B1 | 11/2004 | Edwards et al. | |
| 6,849,073 B2 | 2/2005 | Hoey et al. | |
| 6,852,091 B2 | 2/2005 | Edwards et al. | |
| 6,855,141 B2 | 2/2005 | Lovewell | |
| D509,900 S | 9/2005 | Barnes et al. | |
| 6,989,004 B2 | 1/2006 | Hinchliffe et al. | |
| D538,432 S | 3/2007 | Diener et al. | |
| 2001/0031941 A1 | 10/2001 | Edwards et al. | |
| 2001/0039415 A1 | 11/2001 | Francischelli et al. | |
| 2002/0019612 A1 | 2/2002 | Watanabe et al. | |
| 2002/0058933 A1 | 5/2002 | Christopherson et al. | |
| 2002/0077627 A1* | 6/2002 | Johnson et al. | 606/41 |
| 2002/0103483 A1 | 8/2002 | Edwards | |
| 2002/0111619 A1 | 8/2002 | Keast et al. | |
| 2002/0120261 A1* | 8/2002 | Morris et al. | 606/41 |
| 2002/0151884 A1 | 10/2002 | Hoey et al. | |
| 2002/0177846 A1 | 11/2002 | Mulier et al. | |
| 2002/0183740 A1 | 12/2002 | Edwards et al. | |
| 2002/0198504 A1 | 12/2002 | Risk, Jr. et al. | |
| 2003/0028188 A1 | 2/2003 | Paddock et al. | |
| 2003/0073989 A1 | 4/2003 | Hoey et al. | |
| 2003/0093503 A1 | 5/2003 | Yamaki et al. | |
| 2003/0103932 A1 | 6/2003 | Slepian et al. | |
| 2003/0144656 A1* | 7/2003 | Ocel et al. | 606/41 |
| 2003/0216724 A1 | 11/2003 | Jahns | |
| 2004/0002647 A1 | 1/2004 | Desai | |
| 2004/0082946 A1 | 4/2004 | Malis et al. | |
| 2004/0133194 A1 | 7/2004 | Eum et al. | |
| 2004/0172112 A1 | 9/2004 | Cioanta et al. | |
| 2004/0176984 A1 | 9/2004 | White et al. | |
| 2005/0143728 A1* | 6/2005 | Sampson et al. | 606/41 |
| 2005/0245923 A1 | 11/2005 | Christopherson et al. | |
| 2007/0179496 A1* | 8/2007 | Swoyer et al. | 606/41 |
| 2008/0021486 A1* | 1/2008 | Oyola et al. | 606/169 |

OTHER PUBLICATIONS

Leveillee et al., "Radiofrequency Interstitial Tissue Ablation: Wet Electrode," Journal of Endourology, vol. 17, No. 8, pp. 563-577, 2003.

Related patent application entitled "Delivery of Fluid During Transurethral Prostate Treatment", U.S. Appl. No. 10/424,040, filed Apr. 24, 2003, now abandoned.

Related patent application entitled "Bipolar Virtual Electrode for Transurethral Needle Ablation", U.S. Appl. No. 10/835,193, filed Apr. 29, 2004, now abandoned.

U.S. Patent Application entitled "Portable Therapy Delivery Device With Fluid Delivery", U.S. Appl. No. 11/414,503, filed Apr. 28, 2006, Skwarek et al.

Office Action dated Oct. 9, 2009 for U.S. Appl. No. 11/414,503 (11 pgs.).

Responsive Amendment dated Jan. 8, 2010 for U.S. Appl. No. 11/414,503 (13 pgs.).

Office Action dated Feb. 17, 2009 for U.S. Appl. No. 11/414,503 (11 pgs.).

Responsive Amendment dated Jun. 17, 2009 for U.S. Appl. No. 11/414,503 (13 pgs.).

Final Office Action for U.S. Appl. No. 11/414,503, mailed May 3, 2010, 11 pages.

Notification of Transmittal of the International Search Report and the Written Opinion of the International Searching Authority, or the Declaration for corresponding patent application No. PCT/US2008/053396, mailed Jul. 11, 2008, 11 pages.

Office Action from U.S. Appl. No. 12/938,829, dated Apr. 11, 2011, 15 pp.

Response to Office Action dated Apr. 11, 2011, from U.S. Appl. No. 12/938,829, filed Jul. 7, 2011, 8 pp.

Final office action for U.S. Appl. No. 12/938,829, mailed Sep. 27, 2011, 13 pages.

Response to final office action for U.S. Appl. No. 12/938,829, filed Nov. 22, 2011, 7 pages.

* cited by examiner

FLUID SENSOR FOR ABLATION THERAPY

TECHNICAL FIELD

The invention relates to medical devices and, more particularly, to devices for controlling therapy delivery.

BACKGROUND

Tissue ablation is a surgical technique that may be used to treat a variety of medical conditions, particularly when the treatment requires removing or destroying a target tissue. Medical conditions that can be treated by tissue ablation include, for example, benign prostatic hypertrophy, benign and malignant tumors, and destructive cardiac conductive pathways (such as ventricular tachycardia). Tissue ablation may also be used as part of common surgical procedures, for example, to remove or seal blood vessels.

Typically, ablation therapy involves heating a target tissue with a surgical instrument such as a needle or probe. The needle is coupled to an energy source that heats the needle, the target tissue, or both. Suitable energy sources include, for example, radio frequency (RF) energy, heated fluids, impedance heating, or any combination thereof. The needle may be presented to the target tissue during an open surgical procedure or through a minimally invasive surgical procedure.

The circulation of fluid from and/or around the electrode may be used for tissue irrigation, clearing ablated tissue, or cooling surrounding tissue during ablation therapy. Wet ablation is a type of ablation therapy performed with a wet electrode, which is a needle or probe capable of delivering both RF energy and a conductive fluid to the target tissue. The flow of the conductive fluid may assist in directing the ablation energy and cause a greater volume of tissue to be destroyed, effectively increasing therapy efficacy. Exemplary wet ablation apparatuses and therapy methods are described in U.S. patent application Ser. No. 11/787,211 by Thomas Skwarek et al., entitled, "USER INTERFACE FOR ABLATION THERAPY", and issued on Nov. 1, 2011 as U.S. Pat. No. 8,048,069, which is incorporated herein by reference in its entirety.

SUMMARY

In an ablation apparatus the flow rate of the fluid delivered to the target tissue may be controlled by a pump within an RF energy generator apparatus. In some embodiments, the fluid is conductive, which may allow a greater volume of tissue to be destroyed in a shorter period of time. Since the flow rate and/or delivery pressure of the fluid is directly related to the rate of tissue ablation and the size of the resulting target lesion, effective treatment requires that the practitioner receive timely and accurate information about the flow rate and delivery pressure of the fluid.

In general, the present disclosure is directed to a sensor that detects a fluid parameter indicative of at least one of fluid pressure or flow at a location proximal to the target tissue. For example, the sensor may be located between the pump and the target tissue. At this location proximate to the target tissue, the sensor may provide accurate data regarding fluid delivery to the target tissue and may provide a high degree of therapy safety and/or control.

In one embodiment, the present disclosure is directed to a therapy device comprising a needle that delivers energy to a target tissue to ablate at least a portion of the target tissue, a catheter that houses at least a portion of the needle, wherein a fluid to delivered to the target tissue via the catheter, a housing comprising a handle, wherein the housing is coupled to the catheter, a trigger coupled to the housing that deploys the needle into the target tissue, and a sensor that detects a fluid parameter indicative of at least one of flow or pressure of the fluid, wherein the sensor is located within at least one of the catheter or the housing.

In another embodiment, the present disclosure is directed to a system comprising a generator that generates energy to ablate at least a portion of a target tissue, a needle that delivers the energy to the target tissue, a return electrode that receives energy dispersed from the needle, a catheter that houses at least a portion of the needle, a pump that delivers a fluid to the target tissue via the catheter, a sensor that detects a fluid parameter indicative of at least one of flow or pressure of the fluid, and a processor that analyzes the fluid parameter detected by the sensor located between the pump and the target tissue.

In yet another embodiment, the invention is directed to a method of providing feedback during ablation therapy, the method comprising deploying a needle from a catheter into a target tissue, delivering energy via the needle to ablate at least a portion of the target tissue, delivering a fluid from a pump to the target tissue via the catheter, providing a sensor between the pump and the target tissue, and detecting a fluid parameter indicative of at least one of flow or pressure of the fluid via the sensor.

In yet another embodiment, the invention is directed to a computer-readable medium comprising instructions for causing a programmable processor to deliver energy via a needle to ablate at least a portion of a target tissue, deliver a fluid from a pump to the target tissue via a catheter that houses at least a portion of the needle; and receive data indicative of at least one of flow or pressure of the fluid from a sensor located between the pump and the target tissue.

The details of one or more embodiments of the invention are set forth in the accompanying drawings and the description below. Other features, objects, and advantages of the invention will be apparent from the description and drawings, and from the claims.

DETAILED DESCRIPTION

Tissue ablation may be performed in an open surgical procedure or in a minimally invasive procedure. During a minimally invasive procedure, an ablation device is inserted into a patient until it reaches a target tissue. Since the target tissue cannot be visually inspected during treatment, the clinician usually selects therapy parameters that he or she estimates will yield a preferred lesion size or other treatment result based upon characteristics of the ablation device. The flow rate of fluid delivered to the target tissue may be a therapy parameter selected to yield a particular therapy result, such as a preferred lesion size.

The circulation of fluid from and/or around the electrode may be used for tissue irrigation, clearing ablated tissue, or cooling surrounding tissue. For example, sterile water or another appropriate fluid may be used to cool the urethra during ablation therapy. Delivering a cooling fluid to the urethra may help prevent side effects and/or complications of ablation therapy due to damage to the urethra.

In some embodiments, a conductive fluid, such as saline, is delivered to the target tissue to decrease impedance and allow increased power to be delivered to the target tissue. The use of conductive fluid allows the ablation therapy to be performed at a higher power for a shorter amount of time compared to "dry electrode" therapy that does not utilize a conductive fluid. However, if the therapy is delivered at a high power without an adequate amount of conductive fluid, side effects, such as tissue charring, may occur.

According to the invention, a sensor that detects at least one of flow or pressure is provided. For example, the sensor may be located between the fluid pump and target tissue to help monitor the flow of conductive fluid to the target tissue. Although delivery of a conductive fluid will be described herein for purposes of illustration, the invention is not limited to the delivery of a conductive fluid. For example, a fluid, conductive or nonconductive, may be used for tissue irrigation, clearing ablated tissue, or cooling surrounding tissue.

Figure 1:
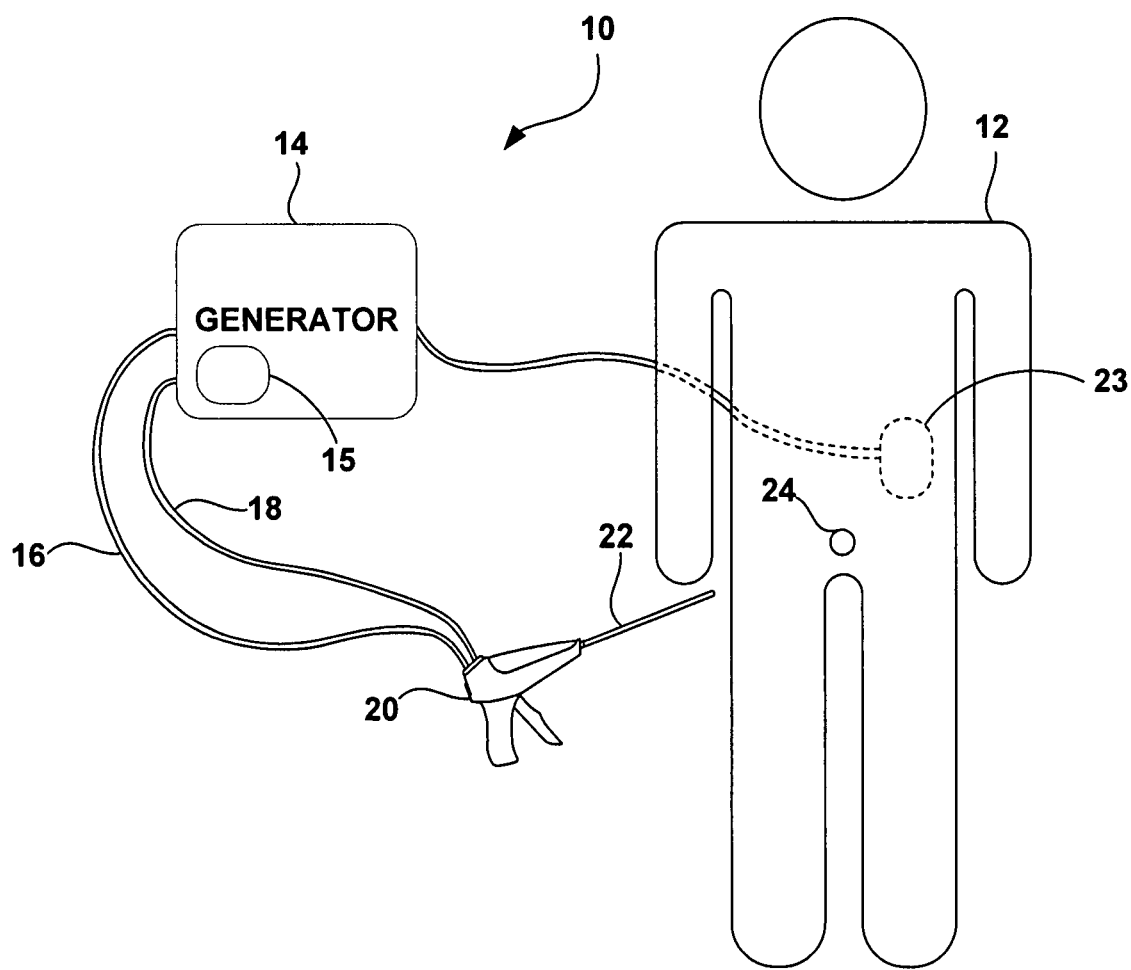
FIG. 1 is a conceptual diagram illustrating an example generator system in conjunction with a patient.

FIG. 1 is a conceptual diagram illustrating an example generator system in conjunction with a patient. As shown in the example of FIG. 1, system 10 may include a generator 14 that delivers therapy to treat a condition of patient 12, such as benign prostatic hypertrophy (BPH).

BPH is a condition caused by the second period of continued prostate gland growth. This growth begins after a man is approximately 25 years old and may begin to cause health problems after 40 years of age. The prostate growth eventually begins to constrict the urethra and may cause problems with urination and bladder functionality. Minimally invasive ablation therapy may be used to treat this condition. A catheter is inserted into the urethra of a patient and directed to the area of the urethra adjacent to the prostate. An ablation needle is extended from the catheter and into the prostate. The clinician performing the procedure selects the desired ablation parameters and the needle heats the prostatic tissue, which may be destroyed and later absorbed by the body. Ablation therapy shrinks the prostate to a smaller size that no longer interferes with normal urination and bladder functionality, and the patient may be relived of most problems related to BPH.

In the exemplary embodiment illustrated in FIG. 1, generator 14 is a radio frequency (RF) generator that provides RF energy to heat tissue of the prostate gland 24. This ablation of prostate tissue destroys a portion of the enlarged prostate caused by, for example, BPH. The RF energy is transmitted through electrical cable 16 to therapy device 20. The energy is then transmitted through a catheter 22 and is delivered to prostate 24 by a needle electrode (not shown in FIG. 1). A fluid may be pumped out of generator 14, through tubing 18, into therapy device 20, and through catheter 22 to or near prostate gland 24. In some embodiments, the fluid is conductive and interacts with the RF energy being delivered by the needle. This "wet electrode" may increase the effective heating area of the needle and increase therapy efficacy. Ground pad 23 may be placed at the lower back of patient 12 to return the energy emitted by the needle electrode.

In the illustrated example, generator 14 is an RF generator that includes circuitry for developing RF energy from an included rechargeable battery or a common electrical outlet. The RF energy is produced within parameters that are adjusted to provide appropriate prostate tissue heating. The RF current is conveyed from generator 14 via electrical cable 16 which is connected to generator 14. The conductive fluid is provided to the needle by pump 15 located within generator 14. In some embodiments, other energy sources may be used in place of RF energy.

The voltage of a fluid pump 15, the current that flows through fluid pump 15, or other operating parameters of fluid pump 15 may be monitored to estimate the flow rate and/or pressure of the fluid delivered by pump 15, and to allow control of pump 15 via a user interface on generator 14. However, several variables may cause the actual flow rate delivered to the target tissue to vary from the flow rate selected at generator 14. As one example, kinking in the tubing carrying the fluid may cause the flow rate at the target tissue site to be lower than the flow rate measured at generator 14.

Therapy energy and other associated functions such as fluid flow may be controlled via a graphical user interface located on a color liquid crystal display (LCD), or equivalent screen of generator 14. The screen may provide images created by the therapy software, and the user may interact with the software by touching the screen at certain locations indicated by the user interface. In this embodiment, no additional devices, such as a keyboard or pointer device, are needed to interact with the device. The touch screen may also enable device operation. In some embodiments, the device may require an access code or biometric authorization to use the device. Requiring the clinician to provide a fingerprint, for example, may limit unauthorized use of the system. Other embodiments of generator 14 may require input devices for control, or the generator may require manual operation or allow minimal computer control of the ablation therapy.

Cable 16 and tube 18 are connected to generator 14. Cable 16 conveys RF energy, and tube 18 conducts fluid from generator 14 to therapy device 20. Tube 18 may carry conductive fluid and/or cooling fluid to the target tissue. In some embodiments, an additional tube (not shown) may carry the cooling fluid used to irrigate the urethra of patient 12.

As previously mentioned, fluid flow may be controlled at generator 14 (e.g., via a graphic user interface located on a color liquid crystal display (LCD), or equivalent screen of generator 14). User input received at generator 14 may be used to control the flow of fluid out of pump 15 within generator 14. However, the flow rate set at generator 14 may not accurately depict the flow of fluid through tube 18. Problems with generator 14 and/or tube 18 may cause the actual flow rate through tube 18 to differ from a flow rate set at generator 14. For example, if pump 15 within generator 14 is improperly connected or there is a kink in tube 18, the actual flow rate of fluid through tube 18 may differ from the flow rate set at generator 14. A sensor (not shown) that measures at least one of flow or pressure may be provided to provide an indication of the actual flow rate of fluid through tube 18. The sensor may be located between generator 14 and prostate 24.

In some embodiments, the sensor is provided within catheter 22. In other embodiments, the sensor is provided within therapy device 20. Positioning the sensor as close to prostate 24 as possible may provide sensed measurements that most accurately detect the actual fluid flow at the target tissue. However, since space is limited within urethral catheter 22, it may be beneficial to include the sensor within therapy device 20. Positioning the sensor within therapy device 20 may provide measurements that accurately reflect the flow of fluid delivered to the target tissue, since most problems that impact fluid flow occur within generator 14 (e.g., pump issues) or between generator 14 and therapy device 20 (e.g., kinks in tube 18).

Therapy device 20 may be embodied as a hand-held device as shown in FIG. 1. Therapy device 20 may include a trigger to control the start and stop of therapy. The trigger may also deploy one or more needles into the target tissue. Attached to the distal end of therapy device 20 is catheter 22. Catheter 22 may provide a conduit for both the RF energy and the fluid. Since catheter 22 enters patient 12 through the urethra, the catheter may be very thin in diameter and long enough to reach the prostate.

The end of catheter 22 may contain one or more electrodes for delivering RF current to the tissue of enlarged prostate 24. Catheter 22 may contain an ablation needle that acts as an electrode for penetrating into an area of prostate 24 from the urethra. In some embodiments, more than one needle may be used in system 10. For example, a second needle may be used to sense tissue properties and/or return the energy emitted by the needle electrode.

When RF energy is being delivered, the target tissue may increase in temperature, which destroys a certain volume of tissue. This heating may last a few seconds or a few minutes, depending on the condition of patient 12. A cooling fluid may be delivered to patient 12 via catheter 22 to help prevent damage to the urethra or other tissues proximate to prostate 24. For example, a cooling fluid may exit small holes in catheter 22 and flow around the urethra. In some embodiments, a conductive fluid may exit small holes in the needle and flow around the electrode. This conductive fluid, e.g., saline, may increase the effective heating area and decrease the heating time for effective treatment. Additionally, ablating tissue in this manner may enable the clinician to complete therapy by repositioning the needles a reduced number of times. The clinician may also use specific therapy parameters (such as flow rate, power, and treatment time) to create a particular size lesion. The selected therapy parameters may be based on data collected for previous ablation procedures, the clinician's experience, and/or the condition of patient 12. In addition, a tissue property measurement (such as tissue temperature or impedance) may be taken to help increase ablation efficacy by accurately controlling the size of the lesion created by the ablation therapy. In this manner, patient 12 may require fewer treatment sessions to effectively treat BPH.

The clinician may choose a flow rate and other therapy parameters to create a lesion of a particular size. If the actual flow rate differs from the target flow rate set at generator 14, the therapy delivered to patient 12 may differ significantly from the intended therapy. For example, if the actual flow rate is significantly higher than the target flow rate set at generator 14, the lesion formed may be significantly larger than intended. If the actual flow rate is significantly lower than the target flow rate set at generator 14, the lesion formed may be significantly smaller than intended. Also, the power of the energy delivered to the target tissue may be selected based on the intended fluid flow. Typically the selected power increases as the selected fluid flow increases, allowing a larger tissue volume to be treated in a shorter time period. If the actual flow rate is significantly lower than the target flow rate, the power may be concentrated on a smaller tissue volume and cause tissue charring. Charred tissue may act as an insulator, making it difficult to heat surrounding tissue and increase the size of the lesion. Also, charred tissue may make re-positioning and removal of catheter 22 from patient 12 difficult.

A sensor located proximate to the target tissue may be used to detect fluid flow issues. The sensor may be positioned between generator 14 and the target tissue. In some embodiments, the sensor may detect the pressure of the fluid as it flows through tube 18. A high pressure reading may indicate that the fluid is stuck within tube 18 or patient 12 is not easily accepting the fluid. A low pressure reading may indicate that very little fluid is being delivered to tube 18, which may indicate, for example, that fluid pump 15 is malfunctioning. If an irregular pressure reading is detected, generator 14 may provide a warning or error message. In one embodiment, the error message is provided on the user interface of generator 14. Alternatively or additionally, an audio indication may be provided. In some embodiments, the therapy delivered to patient 12 is automatically stopped in response to an irregular pressure reading. For example, generator 14 may stop energy delivery via cable 16. Fluid delivery via tube 18 may also be stopped in response to the irregular pressure reading. In other embodiments, the clinician may decide whether or not to stop ablation therapy upon receipt of the error message. In some embodiments, a flow sensor may be provided in addition to or as an alternative to the pressure sensor. In general, a sensor that detects a fluid parameter is provided and an error message may be provided in response to the detected fluid parameter.

In some embodiments, measured flow rate may be compared to a target flow rate set at generator 14. The measured flow rate may be measured directly with a flow sensor or a reading from a pressure sensor may be converted to a measured flow rate using the resistance through tube 18. If the flow rate measured by the sensor substantially differs from the target flow rate, an error message may be provided, as previously described.

In some embodiments, at least one therapy parameter may be adjusted based on the detected fluid parameter. In some embodiments, a change in flow rate of the fluid delivered to the target tissue, a change in a power of the energy delivered to the target tissue, or a treatment time is adjusted based on the detected fluid parameter. For example, if the measured flow rate differs from the target flow rate, pump 15 within generator 14 may be adjusted to pump fluid at an increased or decreased rate so that the measured flow rate substantially equals the original target flow rate set at generator 14. As another example, if the target flow rate (e.g., the originally set flow rate) is lower than the measured flow rate, the initial power setting may be reduced to a-power level appropriate for the measured flow rate. In other embodiments, the detected fluid parameter may be used to gauge ablation progress, and the treatment time may be increased or decreased based on the detected fluid parameter. For example, ablation therapy may be delivered to patient 12 for a specified duration (i.e., treatment time). The treatment time may be increased or decreased if the detected fluid parameter indicates that the ablation progress is behind or ahead of schedule with respect to the initial treatment time. In other embodiments, other therapy parameters may be adjusted based on a fluid parameter detected via a sensor. In some embodiments, the sensor provides constant feedback to generator 14 and adjustments to the therapy parameters are made based on that feedback. A processor may analyze the detected fluid parameter (e.g., compare the measured flow rate to the target flow rate) and generate an error message and/or adjust one or more therapy parameters based on the detected fluid parameter.

As previously described, the sensor may be a flow sensor or a pressure sensor. In embodiments in which one or more therapy parameters may be adjusted based on the detected fluid parameter, a flow sensor may be preferred. Converting pressure readings from a pressure sensor to flow values may introduce some uncertainty, because an assumption regarding resistance through tube 18 must be made during the conversion. However, a pressure sensor may provide a good indicator of how well patient 12 is accepting the fluid. In some embodiments, both a pressure sensor and a flow sensor are provided.

In some cases, therapy device 20 may only be used for one patient. Reuse may cause infection and contamination, so it may be desirable for the therapy device to only be used once. A feature on therapy device 20 may be a smart chip in communication with generator 14. For example, when the therapy device is connected to generator 14, the generator may request use information from the therapy device. If the device has been used before, generator 14 may disable all functions of the therapy device to prevent reuse of the device. Once therapy device 20 has been used, the smart chip may create a use log to identify the therapy delivered and record that the device has been used. The log may include graphs of RF energy delivered to the patient, total RF energy delivered in terms of joules or time duration, error messages created, measured tissue properties, end lesion volume, or any other pertinent information to the therapy.

In some embodiments, catheter 22 may independently include the one or more needles such that different catheters may be attached to therapy device 20. Different catheters 20 may include different configurations of needles, such as lengths, diameters, number of needles, or sensors in the needles. In this manner, a clinician may select the desired catheter 22 that provides the most efficacious therapy to patient 12.

Figure 2:
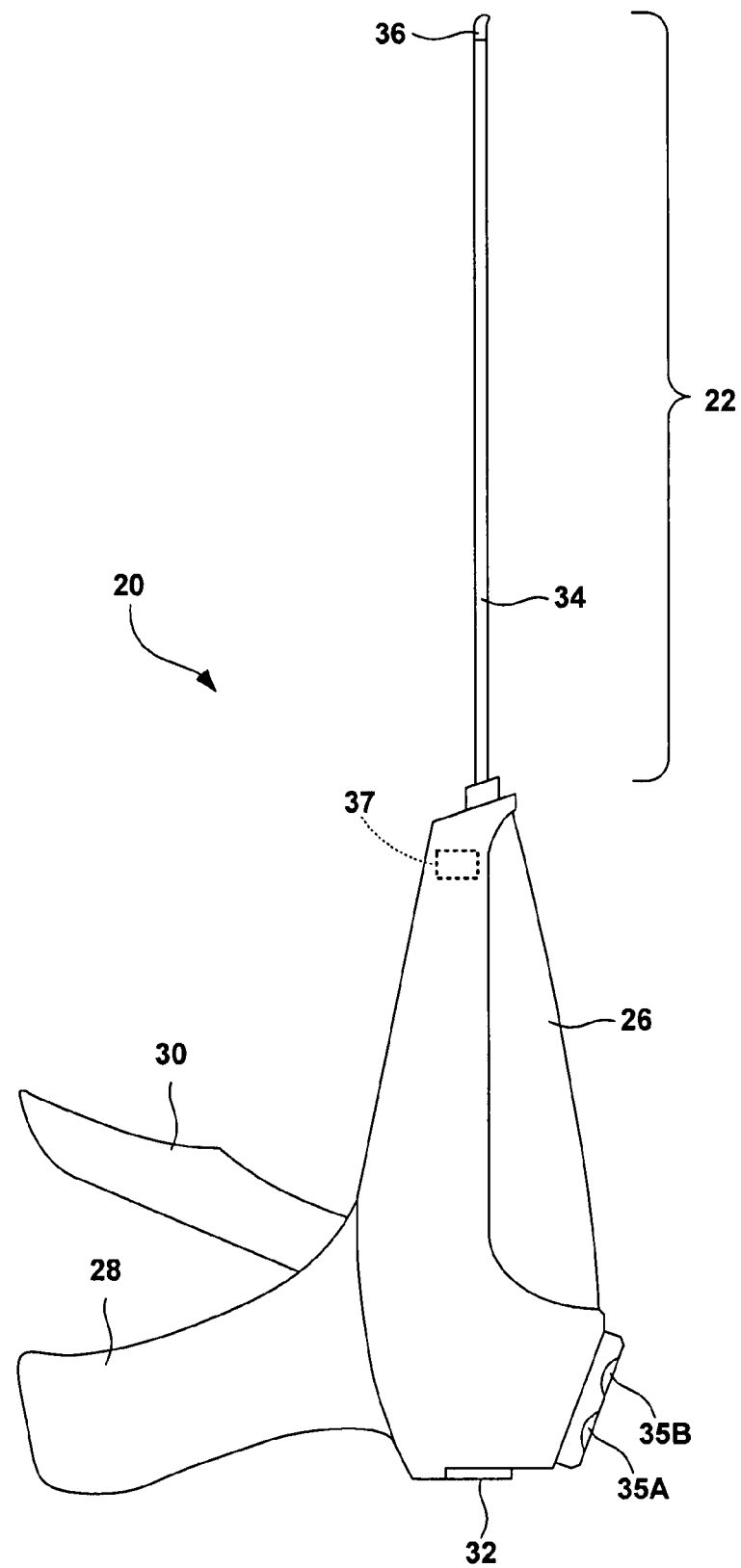
FIG. 2 is a side view of an example hand piece and connected catheter that delivers therapy to target tissue.

FIG. 2 is a side view of an example hand piece and connected catheter that delivers therapy to target tissue. As shown in FIG. 2, therapy device 20 includes housing 26. Housing 26 includes ports 35A and 35B that may be used to couple cable 16 and tubing 18 (FIG. 1) to therapy device 20. Housing 26 is coupled to trigger 30 and includes handle 28. A cystoscope (not shown), may be inserted though axial channel 32 of housing 26 and fitted within catheter 22. Catheter 22 includes shaft 34 and tip 36. A clinician holds handle 28 and trigger 30 to guide catheter 22 through a urethra. The clinician nay use the cystoscope to view the urethra through tip 36 and locate a prostate for positioning the one or more needles (not shown) into prostate 24 from the tip 36. Once the clinician identifies correct placement for the one or more needles, trigger 30 is squeezed toward handle 28 to extend the one or more needles into prostate 24.

As illustrated in FIG. 2, sensor 37 may be located within the hand piece of therapy device 20. Sensor 37 may be a flow meter, such as a turbine flow meter. In other embodiments, sensor 37 may be a pressure transducer, such as a strain gage, variable capacitance, or piezoelectric transducer. In the illustrated embodiment, sensor 37 is positioned proximate to catheter 22. Positioning sensor 37 within the hand piece of therapy device 20 allows sensor 37 to detect flow issues that occur in generator 14 or between generator 14 and sensor 37 (e.g., kinks in tube 18 and problems with pump 15). In alternative embodiments, sensor 37 may be positioned within catheter 22. Regardless of the position of sensor 37, sensor 37 may communicate with generator 14 through a wired or wireless connection. In some embodiments, data may be sent from sensor 37 to generator 14 via cable 16 or another cable.

Housing 26, handle 28 of housing 26, and trigger 30 of therapy device 20 are constructed of a lightweight molded plastic such as polystyrene. In other embodiments, other injection molded plastics may be used such as polyurethane, polypropylene, high molecular weight polyurethane, polycarbonate or nylon. Alternatively, construction materials may be aluminum, stainless steel, a metal alloy or a composite material. In addition, housing 26, handle 28 of housing 26, and trigger 30 may be constructed of different materials instead of being constructed out of the same material. In some embodiments, housing 26, handle 28 of housing 26, and trigger 30 may be assembled through snap fit connections, adhesives, or mechanical fixation devices such as pins or screws. In some embodiments, handle 28 is manufactured as an integral portion of housing 26.

Shaft 34 of catheter 22 may be fixed into a channel of housing 26 or locked in place for a treatment session. Catheter 22 may be produced in different lengths or diameters with different configurations of needles or tip 36. A clinician may be able to interchange catheter 22 in housing 26. In other embodiments, catheter 22 may be manufactured within housing 26 such that catheter 22 may not be interchanged.

Shaft 34 is a rigid structure that is manufactured of stainless steel or another metal alloy and insulated with a polymer such as nylon or polyurethane. Alternatively, shaft 34 may be constructed of a rigid polymer or composite material. Shaft 34 includes one or more channels that house the one or more needles, a cystoscope, and a conduit for conductive fluid. In some embodiments, shaft 34 may also house sensor 37. Tip 36 may be constructed of an optically clear polymer such that the clinician may view the urethra during catheter 22 insertion. Shaft 34 and tip 36 may be attached with a screw mechanism, snap fit, or adhesives. Tip 36 also includes openings that allow the one or more needles to exit catheter 22 and extend into prostate 24.

In some embodiments, housing 26, handle 28 of housing 26, or trigger 30 may include one or more dials or switches to control the deployment of the one or more needles. These controls may finely tune the ability of the clinician to tailor the therapy for patient 12. In some embodiments, shaft 34 and tip 36 may be configured to house two or more needles. For example, multiple needles may be employed to treat a larger volume of tissue at one time and/or provide more accurate feedback relating to the ablation progress.

Figure 3A:
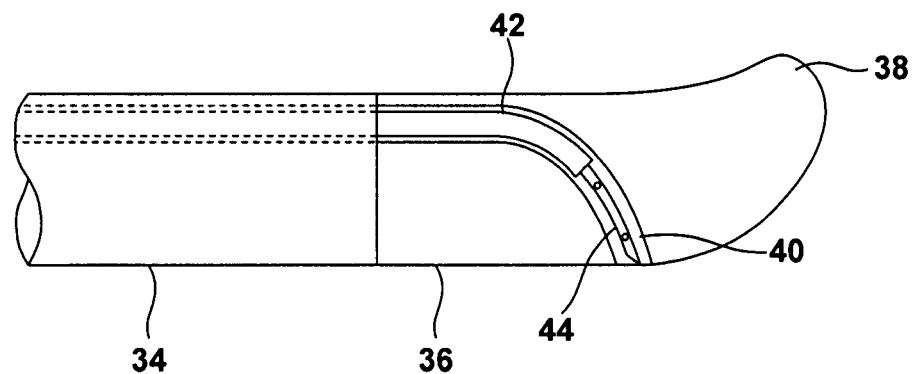
FIG. 3A and 3B are cross-sectional side views of an example catheter tip in which a therapy needle exits to reach the target tissue.
Figure 3B:
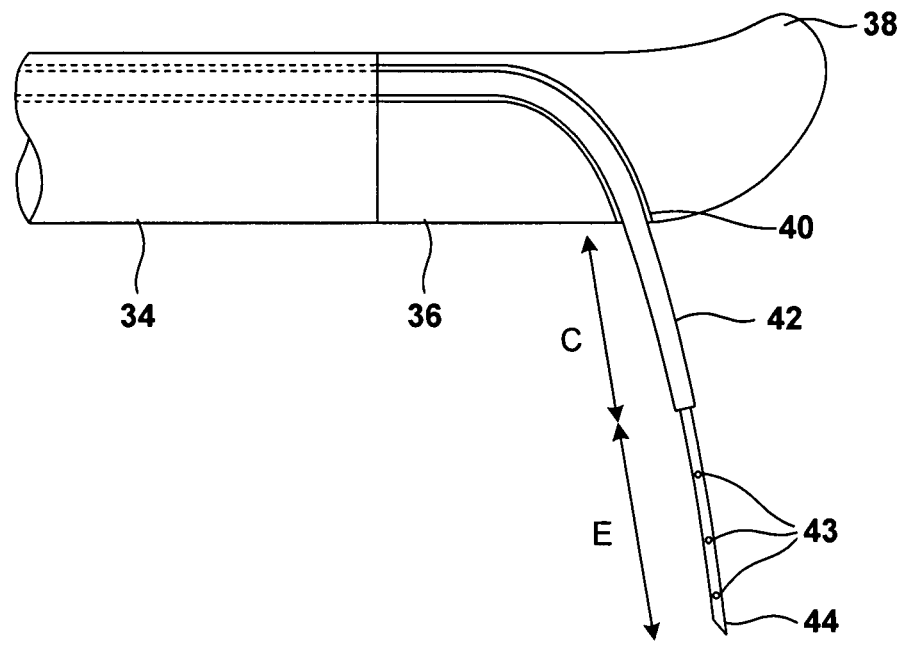

FIGS. 3A and 3B are cross-sectional side views of an exemplary catheter tip in which a therapy needle exits to reach the target tissue. As shown in FIG. 3A, shaft 34 is coupled to tip 36 at the distal end of catheter 22. Tip 36 includes protrusion 38 that aids in catheter insertion through the urethra. Tip 36 also includes channel 40 which allows needle 44 to exit tip 36. Needle 44 is insulated with sheath 42, such that the exposed portion of needle 44 may act as an electrode.

Channel 40 continues from tip 36 through shaft 34. The curved portion of channel 40 in tip 36 deflects needle 44 such that needle 44 penetrates the target tissue from the side of catheter 22. The curvature of channel 40 may be altered to produce different entry angles of needle 44. Needle 44 may not extend beyond the distal end of tip 36. In other words, needle 44 may exit at or near the side of catheter 22, wherein the side is a lengthwise edge substantially facing the wall of the urethra. The wall of the urethra is a tissue barrier as it surrounds catheter 22. In some embodiments, the distal end of needle 44 may stop at a point further from housing 26 than the distal end of tip 36.

As shown in FIG. 3B, needle 44 has been deployed from tip 36 of catheter 22. The exposed length E of needle 44 is variable by controlling the position of sheath 42. The covered length C of needle 44 is the length of the needle outside of tip 36 that is not delivering energy to the surrounding tissue. Exposed length E may be controlled by the clinician to be generally between 1 mm and 50 mm. More specifically, exposed length E may be between 6 mm and 16 mm. Covered length C may be generally between 1 mm and 50 mm. Specifically, covered length C may also be between 5 mm and 7 mm. Once needle 44 is deployed, needle 44 may be locked into place until the ablation therapy is completed.

Needle 44 may be a hollow needle which allows conductive fluid, e.g., saline, to flow from generator 14 to the target tissue. Needle 44 may include multiple holes 43 which allow the conductive fluid to flow into the target tissue and increase the size of the needle electrode. The conductive fluid may also more evenly distribute the RF energy to the tissue to create more uniform lesions. In some embodiments, needle 44 may also include a hole at the distal tip of needle 44. In other embodiments, needle 44 may only include a hole at the distal tip of needle 44. Generator 14 may include a pump 15 that delivers the conductive fluid.

Figure 4:
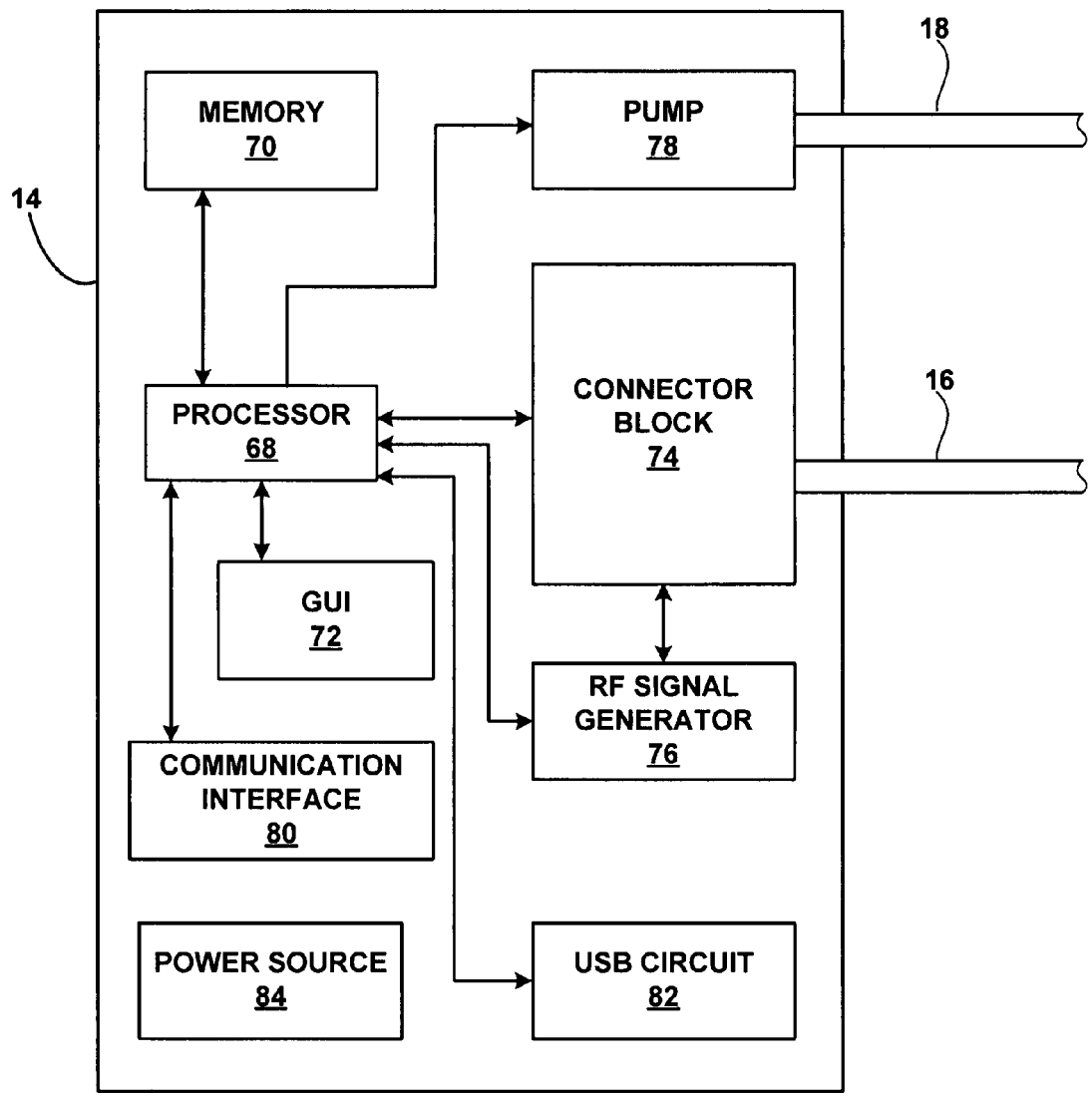
FIG. 4 is functional block diagram illustrating components of an exemplary generator system.

FIG. 4 is functional block diagram illustrating components of an exemplary generator system. In the example of FIG. 4, generator 14 includes a processor 68, memory 70, graphical user interface 72, connector block 74, RF signal generator 76, pump 78, telemetry interface 80, USB circuit 82, and power source 84. As shown in FIG. 7, connector block 74 is coupled to cable 16 for delivering RF energy produced by RF signal generator 76. Pump 78 is coupled to tube 18 and produces pressure to deliver fluid through tube 18.

Processor 68 controls RF signal generator 76 to deliver RF energy therapy through connector block 74 according to therapy parameter values stored in memory 70. Processor 68 may receive such parameter values from graphical user interface 72 or telemetry interface 80 or USB circuit 82. When signaled by the clinician, which may be a signal from therapy device 20 conveyed through connector block 74, processor 68 communicates with RF signal generator 76 to produce the appropriate RF energy. As needed, pump 78 provides fluid to the electrode during wet electrode ablation. Pump 78 may also provide fluid to irrigate the ablation site or cooling surrounding tissue.

Fluid parameters detected by sensor 37 may be received by processor 68 of generator 14 via communication interface 80. Processor 68 may analyze the fluid parameters received from sensor 37 and, if appropriate, generate an error message for display on graphical user interface 72. Additionally or alternatively, processor 68 may stop RF signal generator 76 from delivering therapy to patient 12 upon analysis of the fluid parameters received from sensor 37. In some embodiments, processor 68 may control RF signal generator 76 to deliver RF energy therapy through connector block 74 according to modified therapy parameter values based on the analysis of fluid parameters received from sensor 37. For example, processor 68 may control RF signal generator 76 to deliver RF energy at a modified power. Additionally or alternatively, processor 68 may control pump 78 to deliver conductive fluid at a modified flow rate. Processor 68 may also modify other therapy parameters, such as treatment time, based on analysis of the fluid parameters received from sensor 37.

In a preferred embodiment, the RF signal generator may have certain performance parameters. In this exemplary case, the generator may provide RF energy into two channels with a maximum of 50 Watts per channel. The ramp time for a 50 Watt change in power may occur in less than 25 milliseconds. The output power may be selected in 1 Watt steps. The maximum current to be provided to the patient may be 1.5 Amps, and the maximum voltage may be 180 Volts.

Connector block 74 may contain an interface for a plurality of connections, not just the connection for cable 16. These other connections may include one for a return electrode (e.g., ground pad 23 of FIG. 1 or a second needle), a second RF energy channel, a fluid parameter sensor, and/or a tissue property sensor. Connector block 74 may be a variety of blocks used to diagnose or treat a variety of diseases. All connector blocks may be exchanged and connected to processor 68 for proper operation. Pump 78 may be replaceable by the clinician to replace a dysfunctional pump or allow use of another pump capable of pumping fluid at a different flow rate.

Processor 68 may also control data flow from the therapy. Data such as RF energy produced and fluid flow may be channeled into memory 70 for later retrieval and analysis. Processor 68 may comprise any one or more of a microprocessor, digital signal processor (DSP), application specific integrated circuit (ASIC), field-programmable gate array (FPGA), or other digital logic circuitry. Memory 70 may include multiple memories for storing a variety of data. For example, one memory may contain therapy parameters, one may contain generator operational files, and one may contain measured therapy data. Memory 70 may include any one or more of a random access memory (RAM), read-only memory (ROM), electronically-erasable programmable ROM (EEPROM), flash memory, or the like.

Processor 68 may also send data to USB circuit 82 when a USB device is present to save data from therapy. USB circuit 82 may control any number of USB ports included in generator 14. In some embodiments, USB circuit may be an IEEE circuit when IEEE ports are used as a means for transferring data.

USB circuit 82 may control a variety of external devices. In some embodiments, a keyboard or mouse may be connected via a USB port for system control. In other embodiments, a printer may be attached via a USB port to create hard copies of patient data or summarize the therapy. Other types of connectivity may be available through the USB circuit 82, such as internet access.

Communications with generator 14 may be accomplished by RF communication or local area network (LAN) with another computing device or network access point. This communication is possible through the use of communication interface 80. Communication interface 80 may be configured to conduct wireless or wired data transactions simultaneously as needed by the clinician.

Generator 14 may communicate with a variety of devices to enable appropriate operation. For example, generator 14 may utilize communication interface 80 to monitor inventory, order disposable parts for therapy from a vendor, and download upgraded software for a therapy. In some embodiments, the clinician may communicate with a help-desk, either computer directed or human staffed, in real-time to solve operational problems quickly. These problems with generator 14 or a connected therapy device may be diagnosed remotely and remedied via a software patch in some cases.

Graphical user interface 72 provides an interface between generator 14 and the clinician. Processor 68 controls the graphics displayed on graphical user interface 72 and identifies when the clinician presses on certain portions of the graphical user interface 72, which is sensitive to touch control. In this manner, operation of graphical user interface 72 may be central to the operation of generator 14 and appropriate therapy or diagnosis.

Power source 84 delivers operating power to the components of generator 14. Power source 84 may utilize electricity from a standard 115 Volt electrical outlet or include a battery and a power generation circuit to produce the operating power. In some embodiments, the battery may be rechargeable to allow extended operation. Recharging may be accomplished through the 115 Volt electrical outlet. In other embodiments, traditional batteries may be used.

Figure 5:
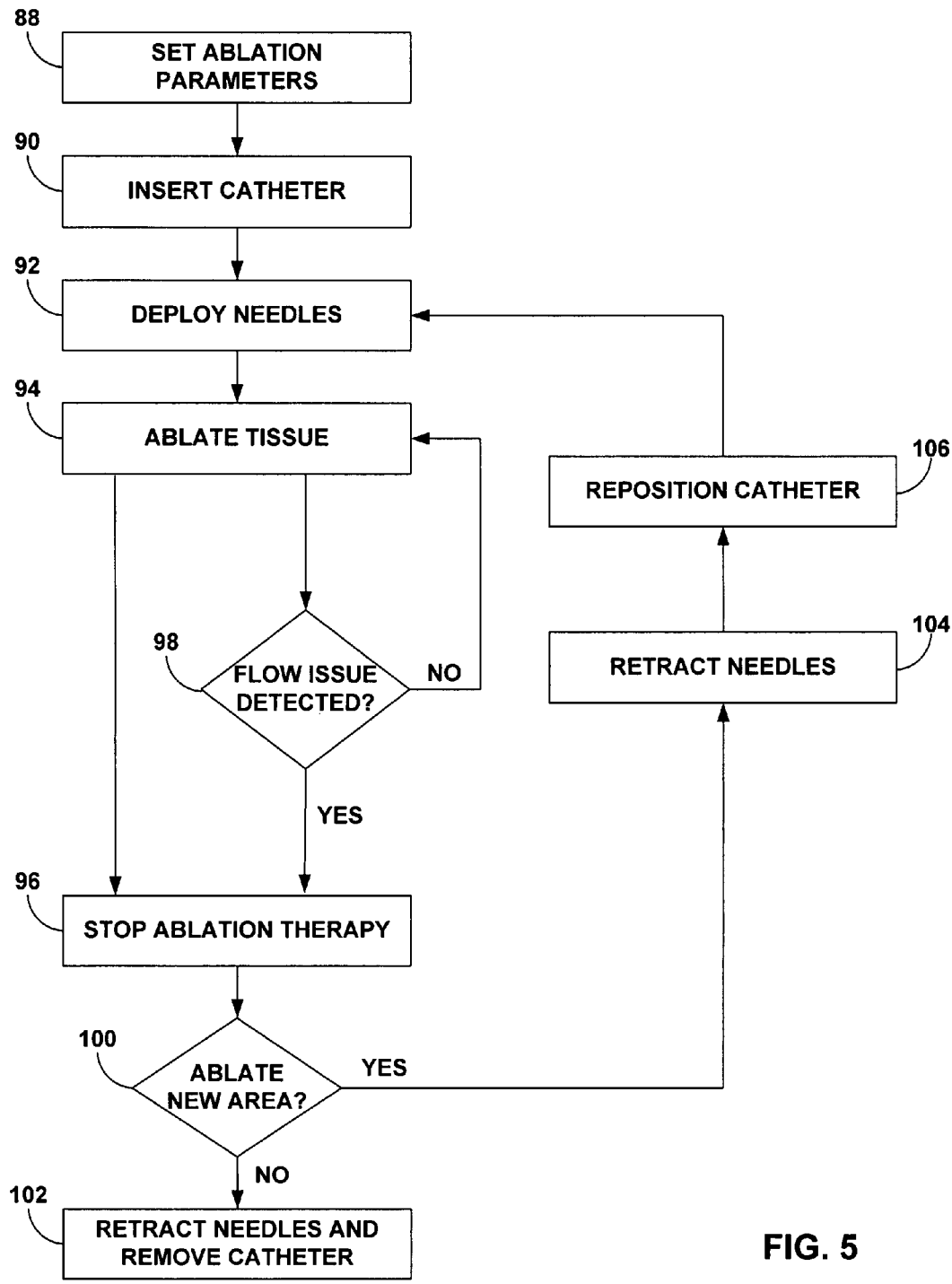
FIG. 5 is a flow diagram illustrating an example technique for delivering tissue ablation therapy utilizing a flow or pressure sensor.

FIG. 5 is a flow diagram illustrating an example technique for delivering tissue ablation therapy utilizing sensor 37. The clinician sets ablation parameters in generator 14 (88). Ablation parameters may include RF power, needle lengths, flow rate of conductive fluid, or other parameters related to the therapy. Selecting a desired catheter 22 configuration may be an ablation parameter as well. The clinician next inserts catheter 22 into the urethra of patient 12 until tip 36 is correctly positioned adjacent to prostate 24 (90). The clinician may use a cystoscope within catheter 22 to guide the catheter. Once correctly positioned, the clinician deploys needle 44 into prostate 24 (92).

The clinician starts tissue ablation by pressing a button on generator 14 or therapy device 20 (94). Fluid is delivered by needle 44. If the clinician is satisfied with the therapy delivered, he or she may stop the ablation therapy (96). Concurrently, sensor 37 monitors the fluid parameter and determines if a flow issue has occurred (98). For example, the fluid parameter detected at sensors 37 may be compared to a threshold as a safety mechanism for the therapy. The threshold may be clinician set or determined based on the power of energy currently being delivered to patient 12. If a flow issue is not detected, generator 14 continues to allow the clinician to ablate tissue (94). If a flow issue is detected, generator 14 may automatically terminate the ablation therapy (96). In other embodiments, generator may additionally or alternatively provide an error message indicating a flow issue has occurred. If a flow issue is detected, generator 14 may not allow the clinician to redeliver RF energy until the flow rate or power is modified.

If the clinician does not want to ablate a new area of prostate 24 (100), the clinician retracts needles 44 and 48 and removes catheter 22 from patient 12 (102). If the clinician desires to ablate more tissue, the clinician retracts needle 44 (104), repositions catheter 22 adjacent to the new tissue area (106), and deploys needle 44 once more (92). Ablation may begin again to treat more tissue (94).

The example technique outlined in FIG. 5 depicts one embodiment of the invention in which sensor 37 provides a safety mechanism for ablation therapy. In alternative embodiments, the fluid parameter is analyzed throughout the tissue ablation procedure and one or more therapy parameters are adjusted based on the analysis. Alternatively, the clinician may disable the fluid parameter feature such that the ablation progress is completely manual and dependent upon the fluid flow rate set at generator 14. In other embodiments, a fluid parameter of a nonconductive fluid (e.g., sterile water used for tissue cooling) is detected.

The preceding specific embodiments are illustrative of the practice of the invention. It is to be understood, therefore, that other expedients known to those skilled in the art or disclosed herein may be employed without departing from the invention or the scope of the claims.

Various embodiments of the invention have been described. These and other embodiments are within the scope of the following claims.

The invention claimed is:

1. A method of monitoring fluid delivered during ablation therapy, the method comprising:
deploying, via a trigger coupled to a housing comprising a handle, a needle from a catheter that houses at least a portion of the needle into a target tissue, wherein the housing is coupled to the catheter;
delivering ablation energy via the needle to ablate at least a portion of the target tissue;
delivering the fluid from a pump to the target tissue via the catheter;
providing a sensor between the pump and the target tissue, wherein the sensor is located within at least one of the catheter or the housing;
detecting, by the sensor, a fluid parameter indicative of at least one of flow or pressure of the fluid;
automatically stopping, by a processor, delivery of the ablation energy in response to the detected fluid parameter exceeding a threshold; and
automatically allowing, by the processor, subsequent redelivery of the ablation energy only after the processor receives user input comprising an adjustment of at least one of a flow rate of the fluid and a power of the ablation energy.

2. The method of claim 1, further comprising displaying an error message on a user interface in response to the detected fluid parameter exceeding the threshold.

3. The method of claim 1, wherein delivering ablation energy via the needle is at least partially controlled by a set of therapy parameters, and wherein at least one therapy parameters of the set of therapy parameters is adjusted based on the detected fluid parameter.

4. The method of claim 3, wherein the adjustment to the at least one therapy parameter comprises a change in a flow rate of the fluid delivered to the target tissue.

5. The method of claim 3, wherein the adjustment to the at least one therapy parameter comprises a change in a power of the ablation energy delivered to the target tissue.

6. The method of claim 3, wherein the adjustment to the at least one therapy parameter comprises a change in a treatment time of the delivered ablation energy.

7. The method of claim 1, further comprising measuring a tissue property via the needle.

8. The method of claim 1, wherein delivering the fluid to the target tissue comprises moving the fluid through a plurality of holes in the needle.

9. The method of claim 1, further comprising retracting the needle after at least a portion of the target tissue is ablated.

10. The method of claim 1, wherein the target tissue is a prostate.

11. The method of claim 1, further comprising:
receiving, by a user interface, the user input comprising the adjustment of at least one of the flow rate of the fluid and the power of the ablation energy; and
receiving, by the processor and from the user interface, the user input.

12. A therapy device comprising:
a needle that delivers ablation energy to a target tissue to ablate at least a portion of the target tissue;
a catheter that houses at least a portion of the needle, wherein a fluid is deliverable to the target tissue via the catheter;
a housing comprising a handle, wherein the housing is coupled to the catheter;
a trigger coupled to the housing that deploys the needle into the target tissue;
a sensor that detects a fluid parameter of at least one of flow and pressure of the fluid, wherein the sensor is located within at least one of the catheter and the housing; and
a processor configured to automatically stop the delivery of the ablation energy in response to the detected fluid parameter exceeding a threshold and automatically allow subsequent redelivery of the ablation energy only after the processor receives user input adjusting at least one of a flow rate of the fluid and a power of the ablation energy.

13. The therapy device of claim 12, wherein the housing comprises a channel that accommodates a cystoscope.

14. The therapy device of claim 12, wherein the housing comprises a first port that couples a tube to the therapy device and a second port that couples a cable to the therapy device, wherein the tube is configured to deliver the fluid to the therapy device, and wherein the cable is configured to deliver the ablation energy to the therapy device.

15. The therapy device of claim 12, wherein the needle comprises a plurality of holes that deliver the fluid to the target tissue.

16. The therapy device of claim 12, further comprising a user interface configured to display an error message in response to the detected fluid parameter exceeding the threshold.

17. The therapy device of claim 12, wherein the processor is configured to adjust, based on the detected fluid parameter, a treatment time of at least one of the delivery of the ablation energy and the subsequent redelivery of the ablation energy.

18. The therapy device of claim 12, wherein the processor is configured to control the delivery of the fluid via the catheter based on the detected fluid parameter.

19. The therapy device of claim 12, wherein the detected fluid parameter is indicative of at least one of a flow issue with a fluid pump or a flow issue between the fluid pump and the sensor.

20. The therapy device of claim 12, wherein the processor is configured to compare the detected fluid parameter to the threshold.

21. The therapy device of claim 12, wherein the threshold is configurable to be set by a clinician.

22. The therapy device of claim 12, wherein the processor is configured to determine the threshold of the fluid parameter based on the power of the ablation energy delivered by the needle.

23. The therapy device of claim 12, further comprising a user interface, wherein the user interface is configured to receive the user input adjusting the at least one of the flow rate of the fluid and the power of the ablation energy, and wherein the processor is configured to receive the user input from the user interface.

* * * * *